United States Patent [19]

Iba et al.

[11] Patent Number: 4,564,273
[45] Date of Patent: Jan. 14, 1986

[54] RETINAL CAMERA

[75] Inventors: Youich Iba; Kouji Inaba, both of Hachiouji, Japan

[73] Assignee: Olympus Optical Co., Ltd., Tokyo, Japan

[21] Appl. No.: 606,001

[22] Filed: May 3, 1984

Related U.S. Application Data

[63] Continuation of Ser. No. 324,952, Nov. 25, 1981, abandoned.

[30] Foreign Application Priority Data

Nov. 26, 1980 [JP] Japan .................. 55-165394

[51] Int. Cl.$^4$ .............................................. A61B 3/14
[52] U.S. Cl. .................................... 351/209; 351/208
[58] Field of Search ............... 351/206, 207, 208, 209, 351/211; 350/422, 444, 507

[56] References Cited

U.S. PATENT DOCUMENTS

| | | | |
|---|---|---|---|
| 1,561,583 | 11/1925 | Bash | 350/507 |
| 3,936,844 | 2/1976 | Matsumura | 351/208 |
| 4,196,979 | 4/1980 | Kohayakawa et al. | 351/208 |
| 4,264,153 | 4/1981 | Ito | 351/208 |

FOREIGN PATENT DOCUMENTS 49-136227  11/1974  Japan .

Primary Examiner—Rodney B. Bovernick
Assistant Examiner—Paul M. Dzierzynski
Attorney, Agent, or Firm—Cushman, Darby & Cushman

[57] ABSTRACT

A retinal camera wherein an auxiliary lens is provided so as to be free to be let into and out of a light path between the position of an image of a retina formed by an objective and a relay lens so that the front eye part of an eye to be examined can be illuminated brightly and uniformly and an image of the front eye part of a high resolution can be obtained at a high magnification. The auxiliary lens has a negative or positive refracting power. The auxiliary lens having a negative refracting power is let into and out of the light path together with an image rotator so that the image of the front eye part can be observed as an erected image.

6 Claims, 8 Drawing Figures

RETINAL CAMERA

This is a continuation, of application Ser. No. 324,952 now abandoned, filed Nov. 25, 1981.

BACKGROUND OF THE INVENTION (a.) Field of the Invention

This invention relates to improvements in retinal cameras and more particularly to a retinal camera provided with an auxiliary optical system.

(b.) Description of the Prior Art

Some retinal camera is provided with an auxiliary optical system so that not only an image of a retina can be observed or photographed but also the front eye part of an eye to be examined can be observed. The optical system of a conventional retinal camera provided with such auxiliary optical system is as shown in FIG. 1. That is to say, a light from a light source 1 for observation is made to form an image in the position of a light source 3 for photographing by a lens 2, passes through a ring slit 4 arranged near the photographing light source 3 and is made to form an image of the ring slit 4 near an annular mirror 6 by a relay lens 5. This illuminating light is further made to form an image near the pupil 8a of an eye 8 to be examined by an objective 7 and then illuminates a retina 8b. An image of the illuminated retina is formed in the position of an image plane 8'b by the objective 7, passes further through a flare preventing stop 9 provided in the aperture of the annular mirror 6, is reflected by a movable mirror 11, is formed on a reticle 12 by a relay lens 10, is reflected by a prism 13 and is then observed through an eyepiece 14.

In the case of photographing, if the photographing light source 3 is made to project a light, the light will pass through the ring slit 4 and will illuminate the retina the same as in the observation. The same as in the case of the observation, the illuminated retina will be made to form an image by the objective 7 and relay lens 10. However, in this case, if the movable mirror 11 is made to spring up to the position 11' shown by the chain line, the image of the retina will be formed on a film surface 15.

On the other hand, in the case of observing the front eye part of the eye to be examined, an auxiliary lens (positive lens) 16 is inserted between the objective 7 and the image 8'b of the retina by this objective 7 so that an image of the front eye part will be formed in the position of the image 8'b of the retina. When this lens 16 is not inserted, the image of the front eye part will be formed near the stop 9 or on the side nearer to the relay lens 10 but, if the auxiliary lens 16 is inserted, the front eye part will be able to be observed and also photographed the same as when the image of the retina is observed.

In the above explained conventional retinal camera, when the auxiliary lens is inserted to observe the front eye part, the lens system combining the objective and auxiliary lens will not be able to be made high in the magnification. Therefore, the front eye part observed through the eyepiece will not be able to have the details seen. Further, in such optical system, in order that the front eye part may be observed at a high magnification, the position of the principal plane of the auxiliary lens must be brought greatly forward (near to the eye to be examined). However, therefore, the formation and shape of the auxiliary lens will become so unreasonable that it will be difficult to well correct the aberrations. For such reasons, too, it is not desirable to increase the magnification of the lens system formed of the objective and auxiliary lens.

Further, as shown in FIG. 2, the image of the stop 9 by the combined lens system of the objective 7 and auxiliary lens 16 is formed as contracted on the side of the eye to be examined near the objective 7. That is to say, the light incident upon the objective 7 from the front eye part 8c will be limited by the image 9' of the stop and the NA (numerical aperture) will be limited as a result. Therefore, by observing the front eye part, the distance between the eye to be examined and the eye of the observer can be adjusted and the optical axes can be aligned but no detailed observation useful for the diagnosis can be made.

SUMMARY OF THE INVENTION

A primary object of the present invention is to provide a retinal camera made to eliminate such defects of the conventional arrangement as are mentioned above.

According to the present invention, this object is attained by arranging an auxiliary optical system so as to be free to be let into and out of a light path between the position of an image of a retina formed by an objective optical system when an eye to be examined is in a proper position and a relay optical system.

According to a preferred formation of the present invention, an optical member for separating an illuminating system and an observing-photographing system from each other is provided within a light path between an objective optical system and relay optical system and the above mentioned auxiliary optical system is arranged so as to be free to be let into and out of the light path between the above mentioned position of the image of the retina and the above mentioned optical member and has a negative refracting power.

According to the retinal camera of the present invention, a front eye part can be observed and photographed with any low to high magnification and a proper NA corresponding to the magnification. Particularly, in the case of the observation and photographing at a high magnification, the NA will be large enough to obtain a high resolving power. Therefore, it is not that the observation of the front eye part can be utilized only for positioning the objective for the eye to be examined as in the conventional retinal camera but that the front eye part can be observed and photographed for such diagnosis as seeing the manner of veins of the front eye part.

Further, in the retinal camera, it is so designed that an image of the vicinity of a cornea or pupil of an eye to be examined may be formed near the optical member for separating the illuminating system including the annular mirror or the like and the observing-photographing system from each other by the objective and therefore the objective corrects the aberrations by using a non-spherical surface or the like so that the image of the front part of the eye to be examined may be favorable. Therefore, the auxiliary lens may only make corrections so that its own aberrations may be favorable. Further, as already described, particularly, in the case of the high magnification, the auxiliary lens will be placed near the stop, therefore no unreasonable movement of the principal plane will be required and no shape hard to correct the aberrations will be required to be made. From these facts, the auxiliary lens is easy to design.

Further, according to the present invention, a very useful retinal camera can be obtained by only adding an auxiliary lens without modifying the optical system of the conventional retinal camera.

According to a preferred formation of the present invention, as an auxiliary lens having a negative refracting power is arranged in front of an annular mirror, a bright image of a uniform brightness can be obtained by illuminating a front eye part through this auxiliary lens.

DESCRIPTION OF THE PREFERRED EMBODIMENTS

Figure 3:
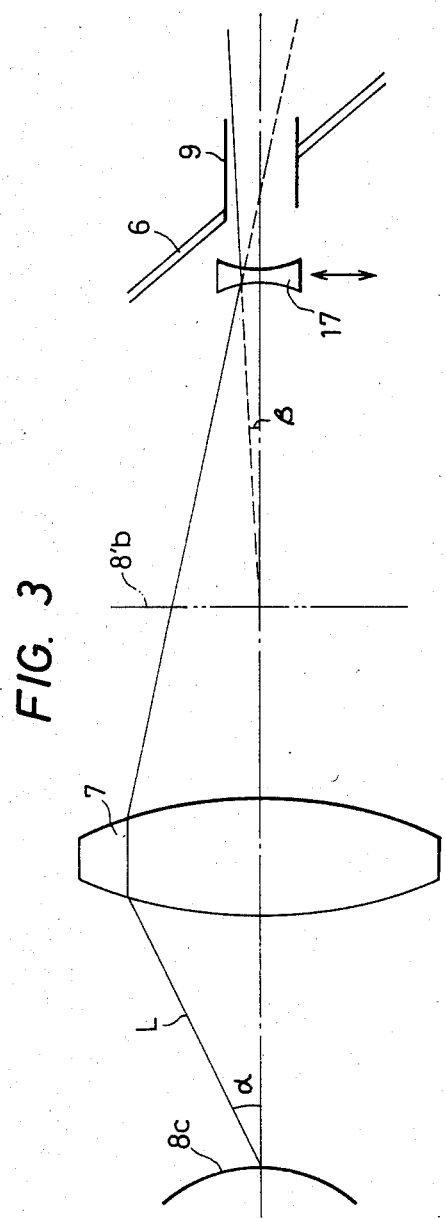
FIG. 3 is an enlarged view of an essential part of an embodiment of an optical system of a retinal camera according to the present invention.

The contents of the present invention shall be explained in detail with reference to the drawings. In the optical system according to the present invention, instead of making it possible to insert a convex lens 16 in a light path between an objective 7 and an image 8'b of a retina by the objective as in the conventional retinal camera shown in FIG. 1, an auxiliary lens is made able to be let into and out of a light path between the image 8'b of the retina by the objective 7 and a relay lens 10. The other formations are substantially the same as in the conventional retinal camera shown in FIG. 1. FIG. 3 is a view of a first embodiment of the present invention showing an essential part from a front eye part 8c of an eye 8 to be examined to an annular mirror 6. In this first embodiment, as illustrated, an auxiliary lens 17 having a negative refracting power is inserted between the position of the image 8'b of the retina and the annular mirror 6. Thus, when the image 8'b of the retina is to be observed or photographed (in case the auxiliary lens 17 is not inserted), the image of the front eye part formed near to or rearward from a stop 9 will be formed as a virtual image near the image 8'b of the retina. Therefore, the front eye part can be observed or photographed the same as in observing or photographing the image 8'b of the retina. Thus, the image of the front eye part can be observed or photographed by inserting the auxiliary lens 17 having a negative refracting power in the light path between the image 8'b of the retina and the annular mirror 6 and the image 8'b of the retina can be observed or photographed by removing this auxiliary lens 17 from the light path.

A light L issued from the optical axis of the front eye part, refracted by the auxiliary lens 17 and passing the edge of an aperture determined by the stop 9 when the auxiliary lens 17 is inserted in the light path in the optical system according to the present invention shall be considered. If the angle made by this light L with the optical axis when it is issued is made $\alpha$ and the angle made by the light refracted by the auxiliary lens 17 with the optical axis is made $\beta$, the magnification of the virtual image of the front eye part 8c formed by the auxiliary lens 17 will be $-\alpha/\beta$. Here, $\beta$ is determined by the diameter of the aperture determined by the stop 9 and the distance between the image 8'b of the retina and the stop 9. Usually the stop aperture is so smaller than the distance between the image 8'b of the retina and the stop that the value of $\beta$ is small. Further, if the auxiliary lens 17 is arranged adjacently to the stop 9 and the axial marginal light is made to pass the edge of the aperture determined by the stop 9 by giving a proper refracting power, the light from the front eye part 8c will be able to be utilized over the entire angle of view of the objective 7. Therefore, $-\alpha/\beta$ can be made large in the value, a high magnification can be obtained and the front eye part can be observed as magnified to be large. If the position of inserting the auxiliary lens 17 is moved toward the image 8'b of the retina from the position shown in FIG. 3 and the refracting power of the auxiliary lens 17 is made to be of a proper desired value so that the virtual image of the front eye part 8c may be formed near the image 8'b of the retina, the value of $\alpha$ will vary and the front eye part 8c will be able to be observed or photographed with a magnification smaller than in the case of FIG. 3. Thus, by varying the arranging position and refracting power of the auxiliary lens 17, the front eye part 8c can be observed or photographed with any low to high magnification.

The NA (numerical aperture) shall be described in the following. If the magnification is represented by M, the incident side NA will be given by the following formula:

Incident side NA = |projecting side NA × M| the projecting side NA in the above formula, that is, sin $\beta$ is a constant determined only by the diameter of the aperture formed by the stop 9 and the distance between the stop 9 and the image plane 8'b of the retina. Therefore, the larger the magnification M, the larger the incident side NA. Therefore, if the observation is made at a high magnification, a high resolution corresponding to it will be obtained and the front eye part 8c will be able to be observed in detail with a resolution corresponding to the magnification M. The outside diameter of the objective 7 is determined by the angle of view and operating distance but, in case image of the front eye part is made to be at a very high magnification when the auxiliary lens 17 is inserted in the light path as shown in FIG. 3, the NA so large as to cover the entire outside diameter of the objective 7 will be taken in to obtain an image of a high resolution.

By the way, the height of the light incident upon the auxiliary lens 17 is so low that the aberrations of the auxiliary lens 17 can be easily corrected.

Figure 4:
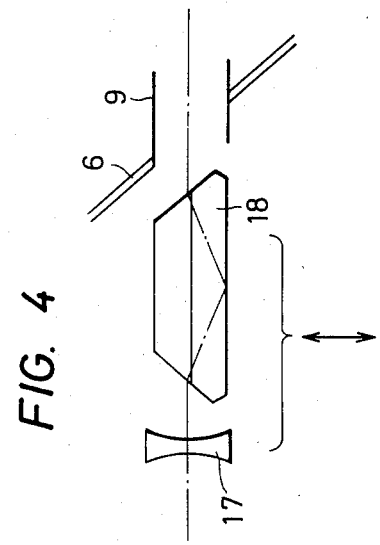
FIG. 4 is an enlarged view of an essential part showing a modification of the embodiment shown in FIG. 3.

In the above explained embodiment, the obtained image of the front eye part is an inverted image. In order to be able to observe or photograph it with an erecting image, as shown in FIG. 4, a proper image rotator 18 may be used. That is to say, if the proper image rotator 18 is arranged in front or rear of the auxiliary lens 17 and the auxiliary lens 17 and image rotator 18 are integrally made to be able to be let into and out of the light path, the image of the front eye part 8c will be able to be observed with an erecting image. There is a retinal camera of a type wherein the observation is not made with an objective but is made on a television monitor with an image photographing tube arranged in an image forming position in an observation system. In the case of the retinal camera of this type, if the image is electrically rotated by 180 degrees, the inverted image will be able to be observed as an erecting image.

Figure 1:
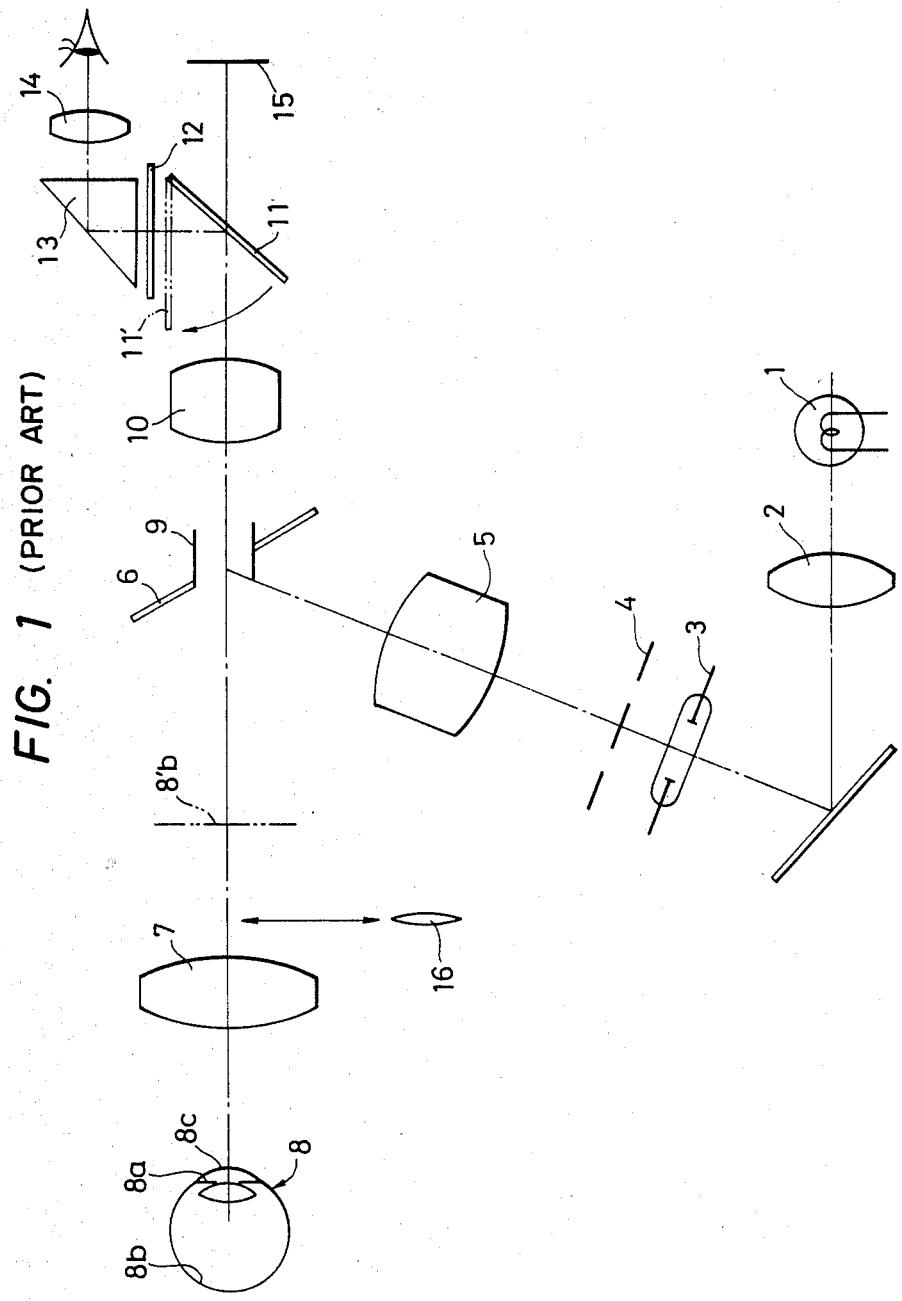
FIG. 1 is a view showing an optical system of a conventional retinal camera.
Figure 2:
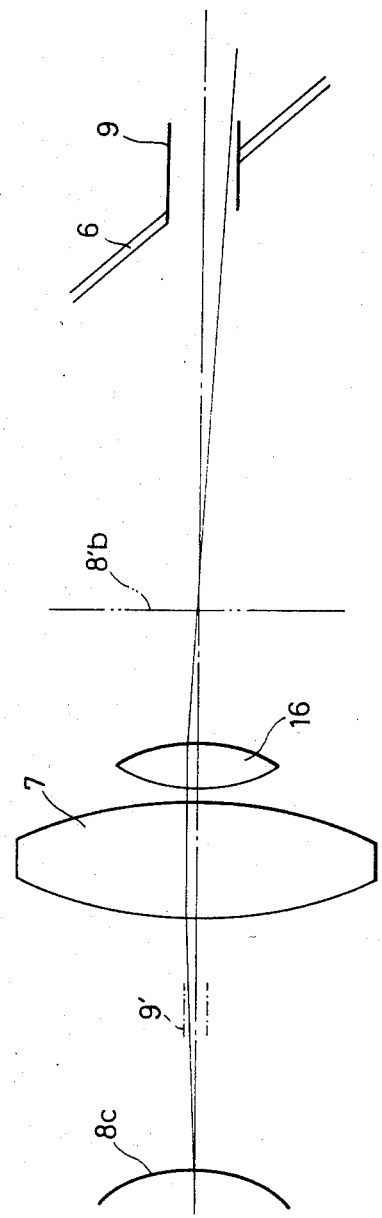
FIG. 2 is a partly enlarged view of the optical system shown in FIG. 1.
Figure 5:
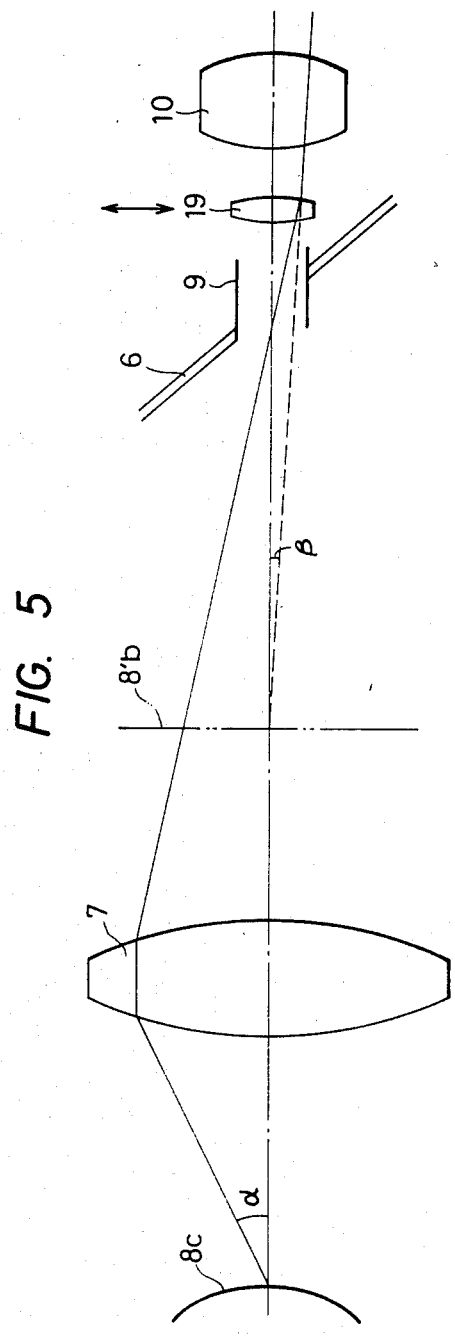
FIG. 5 is an enlarged view of an essential part of another embodiment of the optical system of the retinal camera according to the present invention.

FIG. 5 shows an essential part of a second embodiment of the present invention and the other parts are substantially the same as are shown in FIG. 1. In this embodiment, an auxiliary lens 19 having a positive refracting power is arranged so as to be able to be let into and out of the light path between the annular mirror 6 and photographing relay lens 10. That is to say, by inserting the auxiliary lens 19 in the light path, the image of the front eye part 8c can be observed or photographed at a high magnification. Further, the incident side NA is so large that an image of a front eye part of a high resolution can be obtained. In the case of this embodiment, the observed image is an erecting image.

Generally most retinal cameras are so designed that, when an eye to be examined is in a proper position, the image of the front eye part by an objective will be formed in a stop position arranged near an annular mirror. Therefore, in the above explained respective embodiments, the case that the image of the front eye part is formed in the stop position has been explained. Therefore, in the first embodiment, the auxiliary lens 17 of a negative refracting power is arranged between the image 8'b of the retina by the objective 7 and the annular mirror 6 (stop 9). In the second embodiment, the auxiliary lens 19 of a positive refracting power is arranged between the annular mirror 6 (stop 9) and the relay lens 10. However, the object of the present invention can be attained correctly by arranging the auxiliary lens of a negative refracting power between the image 8'b of the retina by the objective 7 and the image of the front eye part by the objective 7 and the auxiliary lens of a positive refracting power between the image 8'b of the front eye part by the objective 7 and the relay lens 10. Therefore, in a retinal camera in which the image of the front eye part by the objective 7 is formed in a position rearward from the stop 9 (on the relay lens side) and greatly separated from the stop 9, the object of the present invention can be also attained by arranging the auxiliary lens of a negative refracting power rearward from the stop 9.

Figure 6:
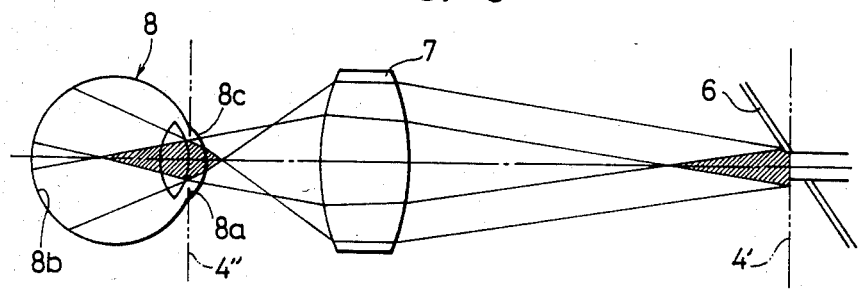
FIGS. 6 to 8 are explanatory views showing respectively different methods of illuminating a front eye part of an eye to be examined.

The method of illuminating the front eye part 8c in the retinal camera of the present invention shall be explained in the following. In the ring illuminating method generally used in the retinal camera, in order to prevent a flare from being caused by a light reflected or dispersed from the front eye part 8c, the front eye part 8c is not so much exposed to a light. That is to say, as shown in FIG. 6, the illuminating light passing through the ring slit 4 forms an image of the ring slit 4 in the position 4', then forms an image 4'' of the ring slit near the iris 8a of the eye 8 to be examined and illuminates the retina 8b. In such ring illuminating method, the front eye part 8c is exposed so little to the light that, even if the front eye part is magnified to be observed, it will be so dark as not to be able to be well observed in some case.

Figure 7:
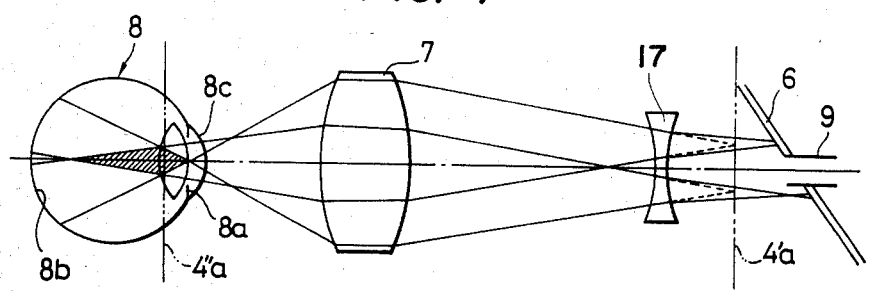

However, in case the auxiliary lens 17 having a negative refracting power is made comparatively large in the diameter and is inserted on the objective 7 side of the annular mirror 6, as shown in FIG. 7, the image 4' of the ring slit in FIG. 6 will become an image 4'a formed in a position moved to the objective 7 side by the auxiliary lens 17. Therefore, the image 4''a of the ring slit by the objective 7 will be formed on the side nearer to the retina 8b of the eye 8 to be examined than the position of the image 4'' in FIG. 6, that is, the position of the iris 8a. That is to say, as evident also from the drawing, in case the auxiliary lens 17 is inserted as in FIG. 7, the center part (near the optical axis) of the front eye part 8c will be also illuminated so well that the front eye part will be able to be uniformly brightly illuminated.

As in the above, in the formation shown in FIG. 3, if the diameter of the auxiliary lens 17 having a negative refracting power is made large enough to cover the illuminating light, the magnified image of the front eye part will be able to be observed and photographed under a bright uniform illumination.

By the way, in the case of this illuminating method, it is necessary to so form the lens that the light reflected by the surface of the auxiliary lens 17 may not pass through the stop 9 to cause a flare or the like.

Figure 8:
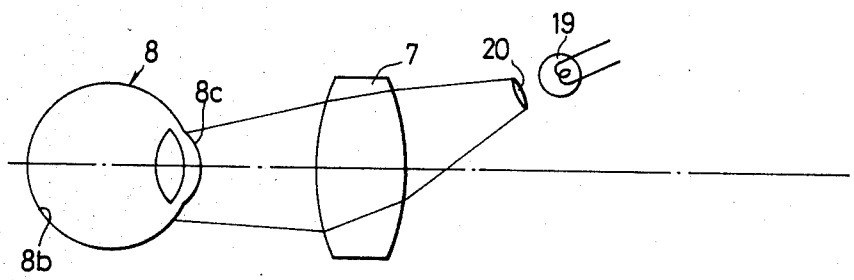

FIG. 8 is of an embodiment wherein the front eye part 8c is illuminated by using another illuminating light source. That is to say, an illuminating light source 19 is arranged in a position deviated from the optical axis of the objective 7 so as not to interfere with the observing light pencil between the objective 7 and annular mirror 6 and so as to illuminate the front eye part through the lens 20 and objective 7.

We claim:

1. A retinal camera, comprising an objective lens for forming an image of a retina of an eye to be examined at a predetermined position and for forming an image of a front eye part of the eye to be examined at a rearward position relative to said image of the retina;
    a relay lens system for re-forming said image of the retina and said image of the front eye part at a predetermined position; and
    an auxiliary lens having a negative refractive power arranged movably in a light path between said image of the retina formed by said objective lens and said image of the front eye part formed by said objective lens, to form, at the position of said image of the retina when said auxiliary lens is inserted in said light path, a virtual image of said image of the front eye part of the eye to be formed by said objective lens.

2. A retinal camera comprising an objective lens for forming an image of a retina of an eye to be examined at a predetermined position and for forming an image of a front eye part of the eye to be examined at a rearward position relative to said image of the retina;
    a relay lens system for re-forming said image of the retina and said image of the front eye part in a predetermined position; and
    an auxiliary lens having a positive refractive power arranged movably in a light path between said image of the retina formed by said objective lens and said relay lens system, to form, at the position of said image of the retina when said auxiliary lens system is inserted in said light path, a virtual image of said image of the front eye part of the eye formed by said objective lens.

3. A retinal camera according to claim 1 wherein said auxiliary optical system comprises an image rotator to convert said image of the front eye part to an erect image.

4. A retinal camera according to any one of claims 1, 2 or 3 wherein said retinal camera further comprises an optical member arranged between said objective lens and relay lens for coupling an illuminating system thereto.

5. A retinal camera according to claim 4 wherein said retinal camera further comprises an observing and photographing system provided with a movable mirror, a light sensitive film placed at the back of said movable mirror and a reticle and eyepiece arranged in turn on the optical axis of a light reflected by said movable mirror.

6. A retinal camera according to claim 5 wherein said illuminating system comprises a light source, a ring slit to be illuminated by said light source and an image forming lens capable of forming an image of said ring slit near said image of the front eye part to be formed through said objective lens.

* * * * *